United States Patent
Hartnett et al.

(10) Patent No.: US 10,247,312 B2
(45) Date of Patent: Apr. 2, 2019

(54) FLUID TRANSFER DEVICE

(71) Applicant: EMD Millipore Corporation, Burlington, MA (US)

(72) Inventors: Jeff Hartnett, West Roxbury, MA (US); Alf Lofving, Torslanda (SE); Lars Hultquist, Alvangen (SE); Jan Davidsson, Kode (SE); Lennart Myhrberg, Alvangen (SE)

(73) Assignee: EMD Millipore Corporation, Burlington, MA (US)

(*) Notice: Subject to any disclaimer, the term of this patent is extended or adjusted under 35 U.S.C. 154(b) by 0 days.

(21) Appl. No.: 15/082,495

(22) Filed: Mar. 28, 2016

(65) Prior Publication Data

US 2016/0208927 A1    Jul. 21, 2016

Related U.S. Application Data

(63) Continuation of application No. 13/827,747, filed on Mar. 14, 2013, which is a continuation of application
(Continued)

(51) Int. Cl.
*F16K 1/12* (2006.01)
*F16K 31/528* (2006.01)
(Continued)

(52) U.S. Cl.
CPC ............ *F16K 1/12* (2013.01); *A61M 39/22* (2013.01); *F04B 39/0005* (2013.01);
(Continued)

(58) Field of Classification Search
CPC . F16K 1/12; F16K 31/528; F16K 7/20; F16K 31/5288; A61M 39/22; F04B 39/0005
(Continued)

(56) References Cited

U.S. PATENT DOCUMENTS 214,367 A    4/1879    Colvin
229,695 A    7/1880    Granger
(Continued)

FOREIGN PATENT DOCUMENTS

CN    101022875 A    8/2007
DE    2161702 A1    6/1973
(Continued)

OTHER PUBLICATIONS

Final rejection dated Jun. 22, 2016 in co-pending U.S. Appl. No. 13/972,301.
(Continued)

*Primary Examiner* — Marina Tietjen
(74) *Attorney, Agent, or Firm* — Nields, Lemack & Frame, LLC (57) ABSTRACT

A disposable device for the sterile transfer of fluids, such as liquids or gases, includes a body, a bore formed through at least a portion of the interior of the body, and a linearly moveable plunger contained within the bore. The body is formed from a rotating section and a stationary section. Partial rotation of the rotating section around a portion of the stationary section and the plunger drives the plunger linearly within the bore, opening and closing the device. The plunger includes at least a first and a second opening, and a fluid channel in the interior of the plunger connecting the first and second openings forming a fluid pathway to downstream components when the device is open. A termination component at one end of the plunger connects to a downstream component. A flange at one end of the body attaches to an upstream component. When the device is closed, the upstream end of the plunger is in alignment with the upstream flange of the body, forming a steamable sterilized in place face and a sterile barrier.

9 Claims, 4 Drawing Sheets

Related U.S. Application Data

No. 12/291,814, filed on Nov. 13, 2008, now Pat. No. 8,690,120.

(60) Provisional application No. 61/003,364, filed on Nov. 16, 2007.

(51) Int. Cl.
*A61M 39/22* (2006.01)
*F04B 39/00* (2006.01)

(52) U.S. Cl.
CPC ....... *F16K 31/528* (2013.01); *Y10T 137/0391* (2015.04); *Y10T 137/8593* (2015.04); *Y10T 137/85986* (2015.04)

(58) Field of Classification Search
USPC ....... 251/215, 347, 341, 343, 344, 346, 318, 251/319, 324–325, 349, 353, 331, 335.2, 251/335.1, 351; 137/614.15; 366/273; 604/411, 249, 256, 533, 537, 905
See application file for complete search history.

(56) References Cited

U.S. PATENT DOCUMENTS

| | | |
|---|---|---|
| 988,378 A | 4/1911 | Olson |
| 1,503,132 A | 7/1924 | Prator |
| 1,585,163 A | 5/1926 | Milner |
| 1,831,457 A | 11/1931 | Larsen |
| 1,852,445 A | 4/1932 | Calkins et al. |
| 2,012,836 A | 8/1935 | Talbot et al. |
| 2,122,991 A | 7/1938 | Polston |
| 2,240,888 A | 5/1941 | Hageline |
| 2,426,808 A | 9/1947 | Auer |
| 2,642,256 A | 6/1953 | Stehlin |
| 2,712,881 A | 7/1955 | Mathisen |
| 2,736,201 A | 2/1956 | Ohlsen et al. |
| 2,767,587 A | 10/1956 | Perkins |
| 2,776,473 A | 1/1957 | Dailey et al. |
| 2,779,350 A | 1/1957 | Owens |
| 2,844,964 A | 7/1958 | Guibert |
| 2,859,932 A | 11/1958 | Mackal |
| 2,865,394 A | 12/1958 | Presley |
| 2,872,817 A | 2/1959 | Pitts |
| 2,952,269 A | 9/1960 | Stehlin |
| 2,994,224 A | 8/1961 | Brown |
| 3,038,485 A | 6/1962 | Hosek |
| 3,039,482 A | 6/1962 | Goldberg |
| 3,097,532 A | 7/1963 | Brown et al. |
| 3,219,047 A | 11/1965 | Kircher, III et al. |
| 3,223,100 A | 12/1965 | Koenig et al. |
| 3,244,376 A | 4/1966 | Thompson |
| 3,260,120 A | 7/1966 | Stilwell |
| 3,276,447 A | 10/1966 | Hamilton |
| 3,319,622 A | 5/1967 | Shiner |
| 3,367,626 A | 2/1968 | Stern |
| 3,390,677 A | 7/1968 | Razimbaud |
| 3,424,181 A | 1/1969 | Morse |
| 3,479,880 A | 11/1969 | Mutter et al. |
| 3,525,350 A | 8/1970 | Hosek |
| 3,621,719 A | 11/1971 | Goodman et al. |
| 3,633,621 A | 1/1972 | Myers |
| 3,638,499 A | 2/1972 | Saint-Andre |
| 3,678,959 A | 7/1972 | Liposky |
| 3,696,932 A | 10/1972 | Rosenberg |
| 3,736,099 A | 5/1973 | Begg et al. |
| 3,747,411 A | 7/1973 | McDermott et al. |
| 3,776,042 A | 12/1973 | Werra et al. |
| 3,779,082 A | 12/1973 | Galloway |
| 3,802,782 A | 4/1974 | Natelson |
| 3,838,707 A * | 10/1974 | Wachowitz, Jr. ....... F16K 41/10 137/312 |
| 3,848,581 A | 11/1974 | Cinqualbre et al. |
| 3,858,449 A | 1/1975 | Singer |
| 3,921,456 A | 11/1975 | Newcomb, Jr. et al. |
| 3,985,332 A | 10/1976 | Walker |
| 4,015,631 A | 4/1977 | Hayes |
| 4,018,059 A | 4/1977 | Hatch |
| 4,034,775 A | 7/1977 | Slagel |
| 4,055,179 A | 10/1977 | Manschot et al. |
| 4,061,709 A | 12/1977 | Miller et al. |
| 4,064,003 A | 12/1977 | Newton |
| 4,094,197 A | 6/1978 | Harris et al. |
| 4,207,922 A | 6/1980 | Andrieux et al. |
| 4,244,224 A | 1/1981 | Conn |
| 4,294,247 A | 10/1981 | Carter et al. |
| 4,296,759 A | 10/1981 | Joslin et al. |
| 4,325,401 A | 4/1982 | Ukai et al. |
| 4,346,609 A | 8/1982 | Diesel |
| 4,353,386 A | 10/1982 | Slagel |
| 4,378,824 A | 4/1983 | Carder |
| 4,423,641 A | 1/1984 | Ottung |
| 4,423,642 A | 1/1984 | Kuboichi |
| 4,454,772 A | 6/1984 | Brunner et al. |
| 4,458,543 A | 7/1984 | Mieth |
| 4,479,393 A | 10/1984 | Shores |
| 4,525,127 A | 6/1985 | Welker |
| 4,527,436 A | 7/1985 | Jones |
| 4,537,593 A | 8/1985 | Alchas |
| 4,557,151 A | 12/1985 | Welker |
| 4,569,236 A | 2/1986 | Kitchen et al. |
| 4,580,452 A | 4/1986 | Masson |
| 4,584,887 A | 4/1986 | Galen |
| 4,587,856 A | 5/1986 | Otis |
| 4,587,887 A | 5/1986 | Shibayama et al. |
| 4,622,457 A | 11/1986 | Bradley et al. |
| 4,630,847 A | 12/1986 | Blenkush |
| 4,657,027 A | 4/1987 | Paulsen |
| 4,669,312 A | 6/1987 | Maurer |
| 4,669,321 A | 6/1987 | Meyer |
| 4,704,910 A | 11/1987 | Conrad |
| 4,826,055 A | 5/1989 | Stull |
| 4,836,236 A | 6/1989 | Ladisch |
| 4,838,877 A | 6/1989 | Massau |
| 4,861,239 A | 8/1989 | Simmons et al. |
| 4,889,692 A | 12/1989 | Holtzman |
| 4,913,185 A | 4/1990 | Mattei |
| 4,941,517 A | 7/1990 | Galloway |
| 4,942,901 A | 7/1990 | Vescovini |
| 4,944,875 A | 7/1990 | Gaignet |
| 4,997,108 A | 3/1991 | Hata |
| 5,058,619 A | 10/1991 | Zheng |
| 5,095,765 A | 3/1992 | Filbey et al. |
| 5,117,872 A | 6/1992 | Yie |
| 5,158,558 A | 10/1992 | Melker et al. |
| 5,161,417 A | 11/1992 | Strong et al. |
| 5,177,872 A | 1/1993 | Lewis et al. |
| 5,246,204 A | 9/1993 | Ottung |
| 5,285,999 A | 2/1994 | Scholz |
| 5,296,197 A | 3/1994 | Newberg et al. |
| 5,360,413 A | 11/1994 | Leason et al. |
| 5,375,477 A | 12/1994 | Neill et al. |
| 5,398,557 A | 3/1995 | Shimizu et al. |
| 5,435,339 A | 7/1995 | Hayes |
| 5,452,746 A | 9/1995 | Hoobyar et al. |
| 5,463,908 A | 11/1995 | Rosolia |
| 5,468,388 A | 11/1995 | Goddard et al. |
| 5,474,546 A | 12/1995 | Ambrisco et al. |
| D366,935 S | 2/1996 | Arthun et al. |
| 5,520,218 A | 5/1996 | Hlavinka et al. |
| 5,525,301 A | 6/1996 | Newberg et al. |
| 5,533,983 A | 7/1996 | Haining |
| 5,535,635 A | 7/1996 | Shaw |
| 5,542,305 A | 8/1996 | Hollinger |
| 5,549,568 A | 8/1996 | Shields |
| 5,585,576 A | 12/1996 | Jaeger |
| D381,067 S | 7/1997 | Karmalm |
| 5,730,418 A | 3/1998 | Feith et al. |
| 5,747,708 A | 5/1998 | Weiberth |
| 5,755,155 A | 5/1998 | Buesing |
| 5,766,462 A | 6/1998 | Jones |
| 5,786,209 A | 7/1998 | Newberg et al. |
| 5,820,614 A | 10/1998 | Erskine et al. |

(56) References Cited

U.S. PATENT DOCUMENTS

| | | |
|---|---|---|
| 5,829,425 A | 11/1998 | Woods et al. |
| 5,865,423 A * | 2/1999 | Barber .................... F16K 41/12 |
| | | 251/335.1 |
| 5,868,433 A | 2/1999 | Matkovich |
| 5,881,997 A * | 3/1999 | Ogawa .................... F16K 41/12 |
| | | 251/335.1 |
| 5,885,255 A | 3/1999 | Jaeger et al. |
| 5,897,526 A | 4/1999 | Vaillancourt |
| 5,911,252 A | 6/1999 | Cassel |
| 5,948,998 A | 9/1999 | Witte et al. |
| 6,009,684 A | 1/2000 | Buesing |
| 6,030,578 A | 2/2000 | McDonald |
| 6,032,543 A | 3/2000 | Arthun et al. |
| 6,056,003 A * | 5/2000 | Madsen .................. F16K 1/446 |
| | | 137/240 |
| 6,068,617 A | 5/2000 | Richmond |
| 6,096,011 A | 8/2000 | Trombley et al. |
| 6,133,022 A | 10/2000 | Newberg |
| 6,145,810 A | 11/2000 | Connoly et al. |
| 6,156,025 A | 12/2000 | Niedospial, Jr. et al. |
| 6,162,206 A | 12/2000 | Bindokas et al. |
| 6,170,800 B1 | 1/2001 | Meloul et al. |
| 6,196,522 B1 | 3/2001 | Yuen et al. |
| 6,210,372 B1 | 4/2001 | Tessmann et al. |
| 6,221,041 B1 | 4/2001 | Russo |
| 6,237,639 B1 | 5/2001 | Jougla et al. |
| 6,254,773 B1 | 7/2001 | Biltoft |
| 6,273,869 B1 | 8/2001 | Vaillancourt |
| 6,306,191 B1 | 10/2001 | McInerney |
| 6,314,987 B1 | 11/2001 | Hay |
| 6,345,640 B1 | 2/2002 | Newberg |
| 6,345,645 B1 | 2/2002 | Kenna et al. |
| D454,173 S | 3/2002 | Almasian et al. |
| 6,354,466 B1 | 3/2002 | Karpisek |
| 6,357,306 B1 | 3/2002 | Jaeger |
| 6,360,794 B1 | 3/2002 | Turner |
| 6,386,137 B1 | 5/2002 | Riche |
| 6,390,127 B2 | 5/2002 | Schick |
| 6,477,906 B1 | 11/2002 | Peterson |
| 6,516,677 B1 | 2/2003 | Suter |
| 6,558,365 B2 | 5/2003 | Zinger et al. |
| 6,568,844 B1 | 5/2003 | Arthun et al. |
| 6,601,823 B2 | 8/2003 | Newberg |
| 6,623,631 B1 | 9/2003 | Graus et al. |
| 6,648,006 B1 | 11/2003 | Ostergaard |
| 6,672,561 B2 | 1/2004 | Kerg et al. |
| 6,699,229 B2 | 3/2004 | Zinger et al. |
| 6,715,624 B2 | 4/2004 | Brockwell |
| 6,779,575 B1 | 8/2004 | Arthun |
| 6,860,162 B1 | 3/2005 | Jaeger |
| 6,871,669 B2 | 3/2005 | Meyer et al. |
| 6,902,144 B2 | 6/2005 | deCler |
| 6,916,012 B2 | 7/2005 | Newberg |
| 7,137,974 B2 | 11/2006 | Almasian et al. |
| 7,195,181 B2 | 3/2007 | Steingass et al. |
| 7,195,182 B2 | 3/2007 | Fischer et al. |
| 7,272,981 B2 | 9/2007 | Bigalke |
| 7,273,550 B2 | 9/2007 | Gutman et al. |
| 7,293,475 B2 | 11/2007 | Furey et al. |
| 7,293,477 B2 | 11/2007 | Furey et al. |
| 7,350,535 B2 | 4/2008 | Leipold et al. |
| 7,473,360 B2 | 1/2009 | Hoffman et al. |
| 7,488,446 B2 | 2/2009 | Meyer et al. |
| 7,578,205 B2 | 8/2009 | Belongia |
| 7,578,936 B2 | 8/2009 | Gaignet et al. |
| 7,597,683 B2 | 10/2009 | Myhrberg et al. |
| 7,661,437 B2 * | 2/2010 | Schulz .................. F16K 41/103 |
| | | 137/312 |
| RE41,169 E | 3/2010 | Arthun |
| 7,722,733 B2 | 5/2010 | Tomasetti et al. |
| 7,753,340 B2 | 7/2010 | Liepold et al. |
| 7,815,362 B2 | 10/2010 | Myhrberg et al. |
| 7,921,740 B2 | 4/2011 | Furey et al. |
| 7,927,316 B2 | 4/2011 | Proulx et al. |
| 7,959,754 B2 | 6/2011 | Arthun |
| 8,029,023 B2 | 10/2011 | Arthun et al. |
| 8,167,480 B2 | 5/2012 | Myhrberg et al. |
| 8,281,961 B2 | 10/2012 | Martin |
| 8,517,998 B2 | 8/2013 | Proulx et al. |
| 8,539,988 B2 | 9/2013 | Guedon |
| 8,544,497 B2 | 10/2013 | Hillier et al. |
| 8,549,935 B2 | 10/2013 | Furey et al. |
| 8,562,572 B2 | 10/2013 | Proulx et al. |
| 8,579,871 B2 | 11/2013 | Proulx et al. |
| 8,646,342 B2 | 2/2014 | Furey et al. |
| 8,690,120 B2 | 4/2014 | Hartnett et al. |
| 8,915,264 B2 | 12/2014 | Hillier et al. |
| 8,919,365 B2 | 12/2014 | Hillier et al. |
| 9,028,779 B2 | 5/2015 | Olivier |
| 9,120,585 B2 | 9/2015 | Olivier |
| 9,150,825 B2 | 10/2015 | Guedon |
| 9,279,100 B2 | 3/2016 | Guedon |
| 9,296,983 B2 | 3/2016 | Guedon |
| 9,482,351 B2 | 11/2016 | Proulx et al. |
| 2001/0022353 A1 * | 9/2001 | Takeda .................... F16K 1/305 |
| | | 251/276 |
| 2002/0024034 A1 * | 2/2002 | Hall ...................... B24C 7/0053 |
| | | 251/62 |
| 2002/0129858 A1 | 9/2002 | Meyer et al. |
| 2003/0188588 A1 | 10/2003 | Jaeger |
| 2005/0006617 A1 * | 1/2005 | Leys ........................ F16K 7/17 |
| | | 251/335.2 |
| 2005/0016620 A1 | 1/2005 | Proulx et al. |
| 2005/0035597 A1 | 2/2005 | Bamberger et al. |
| 2005/0090797 A1 | 4/2005 | Almasian et al. |
| 2005/0132821 A1 | 6/2005 | Furey et al. |
| 2005/0150546 A1 | 7/2005 | Liepold et al. |
| 2005/0285066 A1 | 12/2005 | Huang |
| 2006/0081804 A1 | 4/2006 | Cong |
| 2006/0086922 A1 | 4/2006 | Jensen et al. |
| 2006/0091060 A1 | 5/2006 | Gutman et al. |
| 2006/0142730 A1 | 6/2006 | Proulx et al. |
| 2006/0201263 A1 | 9/2006 | Furey et al. |
| 2006/0211995 A1 | 9/2006 | Myhrberg et al. |
| 2006/0243942 A1 | 11/2006 | Liepold et al. |
| 2006/0272432 A1 | 12/2006 | Belongia |
| 2007/0106264 A1 | 5/2007 | Proulx et al. |
| 2007/0193375 A1 | 8/2007 | Pandori et al. |
| 2007/0212915 A1 | 9/2007 | Strnad et al. |
| 2007/0246674 A1 * | 10/2007 | Kiehne ................. A61M 39/26 |
| | | 251/149.6 |
| 2007/0253287 A1 | 11/2007 | Myhrberg et al. |
| 2008/0000820 A1 | 1/2008 | Mitchell |
| 2008/0022785 A1 | 1/2008 | Furey et al. |
| 2008/0087860 A1 | 4/2008 | Vaillancourt et al. |
| 2008/0103476 A1 | 5/2008 | Schulte |
| 2008/0185552 A1 | 8/2008 | Myhrberg et al. |
| 2008/0277878 A1 | 11/2008 | Arthun et al. |
| 2009/0019952 A1 | 1/2009 | Furey et al. |
| 2009/0054758 A1 | 2/2009 | Dunseath |
| 2009/0101575 A1 | 4/2009 | Alburty et al. |
| 2009/0229671 A1 | 9/2009 | Hartnett et al. |
| 2009/0250157 A1 | 10/2009 | Arthun |
| 2010/0123094 A1 | 5/2010 | Zumbrum |
| 2010/0133459 A1 | 6/2010 | Zumbrum |
| 2010/0154569 A1 | 6/2010 | Guedon |
| 2010/0158759 A1 | 6/2010 | Olivier |
| 2010/0290311 A1 | 11/2010 | Myhrberg et al. |
| 2010/0326212 A1 | 12/2010 | Furey et al. |
| 2011/0155258 A1 | 6/2011 | Zumbrum |
| 2011/0155274 A1 | 6/2011 | Zumbrum |
| 2011/0197989 A1 | 8/2011 | Proulx et al. |
| 2011/0250626 A1 | 10/2011 | Williams et al. |
| 2011/0253233 A1 | 10/2011 | Hillier et al. |
| 2013/0119289 A1 * | 5/2013 | Morris ...................... F16K 7/17 |
| | | 251/331 |
| 2013/0199639 A1 | 8/2013 | Hartnett et al. |
| 2013/0306897 A1 | 11/2013 | Hillier et al. |
| 2013/0312492 A1 | 11/2013 | Hillier et al. |
| 2013/0334450 A1 | 12/2013 | Proulx et al. |
| 2014/0000753 A1 | 1/2014 | Guedon |
| 2014/0014230 A1 | 1/2014 | Guedon |

(56) References Cited

U.S. PATENT DOCUMENTS

| | | | |
|---|---|---|---|
| 2014/0014231 A1 | 1/2014 | Guedon | |
| 2014/0026989 A1 | 1/2014 | Hillier et al. | |
| 2015/0217882 A1 | 8/2015 | Olivier et al. | |

FOREIGN PATENT DOCUMENTS

| | | |
|---|---|---|
| DE | 3215799 A1 | 11/1983 |
| DE | 3633431 A1 | 4/1988 |
| DE | 3701250 A1 | 7/1988 |
| DE | 8812723 U1 | 12/1988 |
| DE | 19901654 A1 | 8/2000 |
| DE | 10039196 A1 | 2/2002 |
| DE | 60310700 T2 | 10/2007 |
| EP | 0103396 A2 | 3/1984 |
| EP | 0107579 A2 | 5/1984 |
| EP | 0154002 A1 | 9/1985 |
| EP | 0468957 A1 | 2/1992 |
| EP | 0508749 A2 | 10/1992 |
| EP | 0510355 A1 | 10/1992 |
| EP | 0576380 A1 | 12/1993 |
| EP | 0684050 A2 | 11/1995 |
| EP | 0691492 A1 | 1/1996 |
| EP | 0858589 A1 | 8/1998 |
| EP | 1008359 A1 | 6/2000 |
| EP | 1231699 A1 | 8/2002 |
| EP | 1321699 A2 | 6/2003 |
| EP | 1329210 A1 | 7/2003 |
| EP | 1370788 A2 | 12/2003 |
| EP | 1499382 A1 | 1/2005 |
| EP | 1548420 A2 | 6/2005 |
| EP | 1962076 A2 | 8/2008 |
| EP | 2060835 A2 | 5/2009 |
| ES | 1028455 U | 1/1995 |
| GB | 943132 A | 11/1963 |
| GB | 1381391 A | 1/1975 |
| GB | 1418046 A | 12/1975 |
| GB | 1463303 A | 2/1977 |
| GB | 1479226 A | 7/1977 |
| GB | 1511240 A | 5/1978 |
| GB | 1573482 A | 8/1980 |
| GB | 2327369 A | 1/1999 |
| GB | 2365511 A | 2/2002 |
| JP | 42-15498 U | 9/1967 |
| JP | 44-4942 U | 2/1969 |
| JP | 45-3461 B | 2/1970 |
| JP | 49-112631 U | 9/1974 |
| JP | 58-131802 U | 9/1983 |
| JP | 59-38278 U | 3/1984 |
| JP | 2-52667 A | 2/1990 |
| JP | 2-71728 A | 3/1990 |
| JP | 2-118276 A | 5/1990 |
| JP | 2-121679 U | 10/1990 |
| JP | 3-141948 A | 6/1991 |
| JP | 6-10845 U | 2/1994 |
| JP | 6-23045 A | 2/1994 |
| JP | 6-78669 U | 11/1994 |
| JP | 6-327772 A | 11/1994 |
| JP | 7-51371 A | 2/1995 |
| JP | 8-502339 A | 3/1996 |
| JP | 8-168535 A | 7/1996 |
| JP | 9-133248 A | 5/1997 |
| JP | 9-154945 A | 6/1997 |
| JP | 9-313896 A | 12/1997 |
| JP | 9-512892 A | 12/1997 |
| JP | 11-141713 A | 5/1999 |
| JP | 11-270705 A | 10/1999 |
| JP | 11-514741 A | 12/1999 |
| JP | 2000-55792 A | 2/2000 |
| JP | 2001-170188 A | 6/2001 |
| JP | 2001-510088 A | 7/2001 |
| JP | 2001-269401 A | 10/2001 |
| JP | 2002-510996 A | 4/2002 |
| JP | 2003-181248 A | 7/2003 |
| JP | 2004-332797 A | 11/2004 |
| JP | 2005-181336 A | 7/2005 |
| JP | 2005-519825 A | 7/2005 |
| JP | 2006-516723 A | 7/2006 |
| JP | 2008-185218 A | 8/2008 |
| JP | 2009-2965 A | 1/2009 |
| JP | 2009-192540 A | 8/2009 |
| JP | 4332106 B2 | 9/2009 |
| SU | 649954 A | 2/1979 |
| WO | 86/02450 A1 | 4/1986 |
| WO | 90/12972 A1 | 11/1990 |
| WO | 91/00215 A1 | 1/1991 |
| WO | 94/08173 A1 | 4/1994 |
| WO | 94/19086 A1 | 9/1994 |
| WO | 95/30856 A1 | 11/1995 |
| WO | 96/30076 A1 | 10/1996 |
| WO | 97/16715 A1 | 5/1997 |
| WO | 98/45188 A1 | 10/1998 |
| WO | 98/50105 A1 | 11/1998 |
| WO | 99/03568 A1 | 1/1999 |
| WO | 99/06089 A1 | 2/1999 |
| WO | 99/26580 A1 | 6/1999 |
| WO | 00/78472 A1 | 12/2000 |
| WO | 03/090842 A1 | 11/2003 |
| WO | 03/090843 A1 | 11/2003 |
| WO | 2005/012775 A1 | 2/2005 |
| WO | 2006/022816 A2 | 3/2006 |
| WO | 2006/026253 A2 | 3/2006 |
| WO | 2008/042285 A2 | 4/2008 |
| WO | 2008/048511 A2 | 4/2008 |
| WO | 2008/136720 A1 | 11/2008 |
| WO | 2010/008395 A1 | 1/2010 |
| WO | 2010/008396 A2 | 1/2010 |
| WO | 2010/122081 A1 | 10/2010 |
| WO | 2012/114105 A1 | 8/2012 |
| WO | 2013/011231 A1 | 1/2013 |

OTHER PUBLICATIONS

Notice of Allowance dated Aug. 8, 2016 in co-pending U.S. Appl. No. 13/972,301.
International Search Report for PCT/US03/12927 dated Aug. 6, 2003, 3 pages.
International Search Report for PCT/US03/13073 dated Aug. 6, 2003, 7 pages.
International Search Report for PCT/US03/12924, dated Aug. 6, 2003, 2 pages.
International Search Report on PCT/US2008/070482, dated Apr. 16, 2009 , 2 pages.
Written Opinion of the International Searching Authority (Appln. No. PCT/US2008/070482, filed Jul. 18, 2008) dated Apr. 16, 2009, 4 pages.
International Search Report on PCT/US2011/021341, dated Sep. 27, 2011, 4 pages.
International Preliminary Examination Report for PCT/US03/12927 dated Feb. 11, 2004, 2 pages.
International Preliminary Examination Report for PCT/US03/12924 dated Jul. 8, 2004, 11 pages.
International Preliminary Report on Patentability (Appln. No. PCT/US2008/070482, filed Jul. 18, 2008) dated Jan. 27, 2011, pp. 1-6.
International Preliminary Report on Patentability (Appln. No. PCT/US2008/070488, filed Jul. 18, 2008) dated Jan. 27, 2011, pp. 1-6.
International Search Report and Written Opinion dated Apr. 3, 2014 in PCT application No. PCT/US2013/075460.
European Search Report EP 1548420 A3, regarding EP App. No. 04029883, dated Mar. 13, 2006, 4 pages.
Japanese Communication, with English translation, dated Feb. 5, 2013 in co-pending Japanese Patent Application No. JP 2011-179614.
Japanese communication , with English translation, dated Jul. 1, 2014 in co-pending Japanese patent application No. JP 2013-161276.
Extended European Search Report dated Dec. 21, 2010 in co-pending European Patent Application No. 08253748.1.
Japanese Communication, with English translation, dated Mar. 26, 2013 in co-pending Japanese Patent Application No. 2008-288424.

(56) References Cited

OTHER PUBLICATIONS

Japanese Communication, with English translation, dated Aug. 21, 2012 in co-pending Japanese patent application No. JP 2010-245357.
Japanese communication, with English translation, dated Feb. 18, 2014 in co-pending Japanese patent application No. JP 2013-032622.
English translation of Chinese Communication dated Aug. 29, 2012 in co-pending Chinese patent application No. CN 201010531386.0.
Chinese Communication, with English translation, dated Dec. 4, 2013 in co-pending Chinese patent application No. 2010105313860.
European communication dated Sep. 17, 2015 in co-pending European patent application No. 10189175.2.
Millipore's Initial Infringement Contentions, Document No. 19, filed Oct. 8, 2009 in the United States District Court for the District of Massachusetts, Civil Action No. 09-10765 DPW, 16 pages.
Gore's Preliminary Non-Infringement Contentions to Plaintiff Millipore Corporation, Document No. 20, filed Oct. 29, 2009 in the United States District Court for the District of Massachusetts, Civil Action No. 09-10765 DPW, 30 pages.
Gore's Preliminary Invalidity Contentions to Plaintiff Millipore Corporation, Document No. 21, filed Oct. 29, 2009 in the United States District Court for the District of Massachusetts, Civil Action No. 09-10765 DPW, 108 pages.
Memorandum and Order, Document No. 70, dated Sep. 20, 2010, in the United States District Court for the District of Massachusetts, Civil Action No. 09-10765-DPW, 59 pages.
Memorandum and Order Denying Millipore's Motion to Alter Judgment and for Reconsideration, U S District Court for the District of Massachusetts, *EMD Millipore Corporation v. W. L. Gore & Associates, Inc.*, Civil Action No. 09-10765-DPW, Document 83, Dated Mar. 20, 2012, 16 pages.
File history of U.S. Trademark Application No. 78/140,217, filed Jul. 1, 2002, 53 pages.
File history of Provisional U.S. Appl. No. 60/375,747 (application filed Apr. 26, 2002), Document 53-2, Case 1:09-cv-10765-DPW, filed May 25, 2010, 50 pages.
File history of Provisional U.S. Appl. No. 60/500,024 (application filed Sep. 4, 2003), 23 pages.
Correspondence from T. Pender to C. Burrell dated Dec. 2, 2011 regarding C.A. No. 11-CV-346-SLR (Bates Stamp GF000001-GF000008), 8 pages.
Documents Produced by Third Party Casella Sales and Marketing Inc., Bates No. CSMI000001 through CSMI000066, 65 pages, Nov. 2011.
Fluid Line Technology Corporation Documents produced in *Gore v. Millipore*, Nov. 28, 2011, Bates # FLT000001 through Bates # FLT000103, 48 pages.
Gore's Prior Art Statement with Exhibits A through I (entire document), U S District Court for the District of Delaware, *W. L. Gore & Associates, Inc. v. EMD Millipore Corporation*, Civil Action No. 11-346-SLR, Dated Dec. 21, 2011, 55 pages.
Gore's First Supplemental Response to Millipore's First Set of Interrogatories [Interrogatory Nos. 11, 15 and 16] dated Nov. 1, 2011, United States District Court for the District of Delaware, Civil Action No. 11-346-SLR, 86 pages.
Gore's Third Supplemental Response to Millipore's First Set of Interrogatories [Interrogatory No. 11], Civil Action No. 11-346-SLR, United States District Court for the District of Delaware, dated Dec. 21, 2011, part 1—pp. 1-43; part 2—pp. 44-85 with Exhibits A-E (334 pages), Exhibits F-G (115 pages) and Exhibits H-I (114 pages). (Note due to the size limitations this is uploaded into 5 parts).
Gore's Fourth Supplemental Response to Millipore's First Set of Interrogatories [Interrogatories Nos. 11 and 12], Civil Action No. 11-346-SLR in the USDC for the District of Delaware, dated May 9, 2012, 172 pages.
Millipore's List of Claim Terms to Be Construed and Proposed Constructions, U S District Court for the District of Delaware, *W. L. Gore & Associates, Inc. v. EMD Millipore Corporation*, Civil Action No. 11-346-SLR, Dated May 30, 2012, 8 pages.
Gore's List of Claim Terms and Proposed Constructions, U S District Court for the District of Delaware, *W. L Gore & Associates, Inc. v. EMD Millipore Corporation*, Civil Action No. 11-346-SLR, Dated May 30, 2012, 4 pages.
Millipore's Responsive Constructions of Claim Terms, U S District Court for the District of Delaware, *W. L. Gore & Associates, Inc. v. EMD Millipore Corporation*, Civil Action No. 11-346-SLR, Dated Jun. 20, 2012, 5 pages.
Gore's List of Responsive Claim Constructions, U S District Court for the District of Delaware, *W. L. Gore & Associates, Inc. v. EMD Millipore Corporation*, Civil Action No. 11-346-SLR, Dated Jun. 27, 2012, 8 pages.
Gore's Motion for Leave to Amend Its Complaint for Declaratory Judgment, US District Court for the District of Delaware, *W. L. Gore & Associates, Inc. v. EMD Millipore Corporation*, Civil Action No. 11-346-SLR-MPT, Document 71, Dated Aug. 8, 2012, 3 pages.
Exhibits 1 and 2 to Gore's Motion for Leave to Amend Its Complaint for Declaratory Judgment, US District Court for the District of Delaware, *W. L. Gore & Associates, Inc. v. EMD Millipore Corporation*, Civil Action No. 11-346-SLR-MPT, Document 75, Redacted-Public Version, Dated Aug. 15, 2012, 241 pages.
Plaintiff Gore's Brief in Support of Motion for Leave to Amend Its Complaint for Declaratory Judgment, US District Court for the District of Delaware, *W. L. Gore & Associates, Inc. v. EMD Millipore Corporation*, Civil Action No. 11-346-SLR-MPT, Document 76, Dated Aug. 15, 2012, Redacted—Public Version, 23 pages.
Preliminary Noninfringement and Invalidity Disclosures of Allpure Technologies, Inc., Document 22, filed Jul. 20, 2011 in the United States District Court for the District of Massachusetts, Civil Action No. 11-cv-10221-DPW, 15 pages.
AESSEAL Environmental Technology P04U and PO5U Single Bellows Component Seal Range, Jan. 2006, (Exhibit 4 to the Affidavit of Alexander H. Slocum, Ph.D., US District Court for the District of Massachusetts, *EMD Millipore Corporation v. AllPure Technologies, Inc.*, Civil Action No. 1:11-cv-10221-DPW,Document 66-4, dated May 2, 2012), 5 pages.
Purdue University—School of Mechanical Engineering—International Compressor Engineering Conference, article by J. W. Abar, "End Face Seals for Air-Conditioning Compressors", 1972 (Exhibit 5 to the Affidavit of Alexander H. Solcum, Ph.D, US District Court for the District of Massachusetts, *EMD Millipore Corporation v. AllPure Technologies, Inc.*, Civil Action No. 1:11-cv-10221-DPW,Document 66-5, dated May 2, 2012), 15 pages.
Memorandum and Order regarding Claim Construction, U S District Court for the District of Massachusetts, *EMD Millipore Corporation v. Allpure Technologies, Inc.*, Civil Action No. 11-10221-DPW, Document 81, Dated Oct. 11, 2012, 34 pages.
Allegheny Bradford Corporation's Objections and Responses to Subpoena, Civil Action No. 1:11-cv-00346-SLR, dated Dec. 15, 2011 in the USDC for the District of Delaware, and Bates # ABC00001 through Bates # ABC000012, 19 pages.
Photographs (7 photos) of the Millipore commercially needleless sampling device; available at least as of Feb. 14, 2012, 7 pages.
Photographs (3 photos) of the Millipore Opticap XLT base, commercially available in 2002, no earlier than Jan. 1, 2002, 3 pages.
Photographs (3 photos) of the Millipore Opticap XL 300, commercially available in 2002, no earlier than Jan. 1, 2002, 3 pages.
Brief for Plaintiff-Appellant, US Court of Appeals, Appeal Nos. 2011-1029, 2012-1371, *EMD Millipore Corporation v. W. L. Gore & Associates, Inc.*, Document 40, dated Jul. 25, 2012 and filed Jul. 27, 2012, 147 pages, submitted in 2 parts.
Brief of Defendant—Appellee W. L. Gore & Associates, Inc., US Court of Appeals, Appeal Nos. 2011-1029, 2012-1371, *EMD Millipore Corporation v. W. L. Gore & Associates, Inc.*, Document 52, filed Oct. 9, 2012, 75 pages.
Reply Brief for Plaintiff—Appellant, US Court of Appeals, Appeal Nos. 2011-1029, 2012-1371, *EMD Millipore Corporation v. W. L. Gore & Associates, Inc.*, Document 57, Dated Nov. 9, 2012, 42 pages.

(56) References Cited

OTHER PUBLICATIONS

About Fluid Line Technology, http://www/fluidlinetech.com/aboutus.html, dated May 8, 2012 and Oct. 30, 2009, 35 pages.
Allegro Single-use Systems—Recommended Capsule Filters and Membranes, http://www.pall.com/main/Biopharmaceuticals/Product.page?id-48022 and http://www.pall.com/variants/print/biopharm_48022.asp, dated May 8, 2012 and Oct. 30, 2009, 51 pages.
AllPure Takeone Aseptic Sampling System Overview, 2 pgs. (Deposition Exhibit dated Nov. 12, 2012).
Tingley, S., "Plastic factory: Disposable biopharmaceutical manufacturing takes a giant leap forward", Alternative Manufacturing, Clean Rooms, pp. S4-S9, (Feb. 2003), 6 pages.
Tingley, S., "Plastic factory, Part II: The final pieces of the disposable puzzle", Alternative Manufacturing, Clean Rooms, pp. 12-14 (Jun. 2003), 4 pages.
ASI Life Sciences, three 60, Single Use Aseptic Sampling System, www.asisus.com, Jan. 10, 2013, 8 pages.
Wendt, D., "BioTrends: Disposable Processing Systems: How Suppliers Are Meeting Today's Biotech Challenges from Fluid Handling to Filtration", Biopharm International, p. 18 (Jul. 2003), 7 pages.
Haughney, H. and H. Aranha, "Disposable Processing Gains you a Competitive Edge: Enhancing Manufacturing Capacity with Disposable Filters, Connectors, and Membrane Chromatagraphy", Biopharm International, p. 50 (Oct. 2003), 7 pages.
Casella Sales & Marketing Inc., CSMI Sample Valves. Datasheet [online]. Retrieved from the Internet: www.casellasales.com (2 pages), product offered online as early as Aug. 2008, according to URL search performed on http://web.archive.org.
Greene, R., et al., "Disposable Equipment: A Mainstay in Bioprocessing", Chemical Engineering Progress, vol. 98, Issue 11, (Nov. 2002), 9 pages.
Haughney, H., et al., "Taking Disposable Processing to the Next Level", Clean Rooms, (Jun. 2004), 5 pages.
Colder Products—Quick Couplings & Fittings for Industrial Applications—Industrial Products, http://www.colder.com/Markets/Industrial/IndustrialProducts/tabid/821/Default.aspx?ProductId=22, dated Oct. 30, 2009, 17 pages.
Daily Business Briefing—"Entegris Introduces the First All Teflon PFA/Process Tee Valve", dated Apr. 16, 2002, 2 pages.
ESP Sanitary Sample Valves Operation and Maintenance Instructions dated Nov. 1995 (WLG-DEL00039664-WLG-DEL00039678), Millipore Corporation, 16 pages.
Entegris Impact Asymmetric Disposable Filters, Product Information brochure, 4414-5723ENT-0511, 2006, 6 pages.
Entegris Impact Mini Disposable Filters, Product Information brochure, 4414-2646ENT-1006, 2006, 4 pages.
Fluid Line Technology Corporation, FLT Bleed/Sample Valve Maintenance, Nov. 10, 2008. Datasheet [online], Fluid Line Technology. Retrieved from the Internet: www.fluidlinetech.com (1 page).
Sanitary Inline Bleed and Sample Valves. Datasheet [online], Fluid Line Technology, Retrieved from the Internet: www.fluidlinetech.com (1 page), document created on Mar. 2, 2009 according to document properties.
Fluid Line Technology Corporation, Product Catalog, 32 pages, Bates No. FLT000003-FLT000034, on information and belief available as of about Nov. 2009.
Gore Single-Use Valve, for Steam-in-Place Applications, 4 pgs. 2009.
Gore STA-PURE Fluid Sampling System, For Single-Use Aseptic Applications, Secure Sampling for Bioprocessing Fluids, Dec. 2008, 4 pages.
ITT Dualrange Control Valve. Data Sheet [online], Pure-Flo. Retrieved from the Internet: www. ittpureflo.com (2 pages), document created Jan. 12, 2007 according to document properties.
ITT Sample & Bleed Valves. Datasheet [online], ITT Corporation, 2006. Retrieved from the Internet: www.ittpureflo.com (4 pages).

Block, S.S., Disinfection, Sterilization, and Preservation (Fourth Edition), Chapter 11, Alcohols, pp. 191-203, by Larson, et al., Lea & Febiger, ISBN:0-8121-1364-0, 1991 (only the year was cited on the publication), 15 pages.
Lynx ST Connectors http://www.millipore.com/catalogue/module/c9131 dated Oct. 30, 2009, 9 pages.
Lynx ST Connectors, Millipore Data Sheet, Lit. No. 051750EN00, Rev. E, May 2008, 4 pages.
Lynx Trademark Reg. No. 2,831,931, first use Apr. 1, 2003, registered Apr. 13, 2004, 3 pages.
Guidelines for Using the Lynx ST Connector. Technical Brief [online], Millipore Corporation, 2008. Retrieved from the Internet: www/millipore.com (2 pages).
International Application No. PCT/US03/13073, filed Apr. 25, 2003, and Request for Express Abandonment of U.S. Appl. No. 10/423,131, filed Sep. 11, 2003, 56 pages.
Microbiological Analysis (Sampling Equipment)—Sampling Ports, p. 130, 1989 (only the year is available for this publication).
MicropreSure Sanitary Sampling Valves, Millipore Data Sheet, Lit. No. DS1006EN00, May 2005, 4 pages.
"Connecting the Sanitary Flange," Datasheet [online], Millipore Corporation, 2007 (pp. 1-2).
Millipore Express SHF Hydrophilic Cartridge Filters, Data Sheet, May 16, 2013, www.millipore.com/catalogue, 2 pages.
Millipore, Hydrophilic Durapore Cartridges and Capsules User Guide, Lit. No. RF 1510EN00, Jan. 2002, 56 pages.
Millipore, Milliflex-P Sanitary Sampling Valves, Operation and Maintenance Instructions, Jul. 2006, 17 pages.
Millipore Corporation, Milli-Q Direct Water Purification System brochure, Lit. No. PB1032EN00, Jan. 2012, 8 pages.
Millipore Corporation, Milli-Q Advantage A10 Water Purification Systems brochure, Lit. No. PB0001EN00, 2013, 12 pages.
NovAseptic—How to Use NA sampling system, http://www.novaseptic.se/main.asp?typ=6, dated Feb. 13, 2002, 2 pages.
NovAseptic, Novaseptum Liquid Sampling System—Totally Enclosed System/ No Cross Contamination/ Presterilized Disposable Unit/ Pyrogen Free, p. 1-4, Feb. 2003.
Millipore Publication, NovAseptic, NovaSeptum Liquid Sampling System, dated Nov. 2001, P75185, Rev. B (Bates stamp—WLG-DEL00040809-WLG-DEL00040813), 6 pages.
NovaSeptum sampling systems, EMD Millipore Data Sheet, Jun. 2012, Lit. # DS0050EN00, Rev. E., 10 pgs.
NovaSeptum sampling systems, Merck Millipore Data Sheet, Apr. 2013, Lit. # DS0050EN00, Rev. H., 10 pgs.
Millipore, NovaSeptum AV Sterile Sampling System, for liquid sampling, User Guide, Lit. No. 00000069TP, Rev. A., Jun. 2006, 2 pages.
Opticap Valve: Millipore Application Note, Jul. 2000, "Gamma Compatible Sterilizing Grade Filter Capsules for Use with Disposable Manufacturing Containers"; 6-pages.
Opticap Vent; Millipore Data Sheet, Apr. 2005, "Gamma Compatible Sterilizing-grade Durapore 0.1 um and 0.22 um Filters", 8-pages.
Opticap3; Millipore Corporation, Nov. 2001, "Opticap TM Capsules with Millistak+™. Media User Guide", 4-Pages.
Millipore Opticap XL and XLT Disposable Capsules, Millipore Corporation, Lit. No. PB1700EN00, Rev. B, Jun. 2004, 4 pages.
Pharmaceutical Engineering, vol. 23, No. 3, May/Jun. 2002, pp. 1-8, "Single-Use Disposable Filling for Sterile Pharmaceuticals", Belongia, et al.
Janetschek, R., "Capsule Filters & Disposable Sterile Processing Systems", Pharmaceutical Processing, vol. 18, No. 11, p. 8 (Jan. 2001), 4 pages.
"New quality of data for bioprocessing bags. (Application Area)." Pharmaceutical Processing, Jan. 2002, Charter Medical, Ltd., Bioprocess Products, Retrieved from the Internet on Feb. 16, 2010 from accessmylibrary: <URL: http://www.accessmylibrary.com/coms2/summary_0286-25022745_ITM>, pp. 1-2.
Pharmenta AptiPort Sampling Valve, http://www.web.archive.org/web/20031029084907/http://www.pharmenta.com/aptiport.htm, 1 page, last modified Mar. 29, 2004, retrieved from internet May 8, 2012.

(56) References Cited

OTHER PUBLICATIONS

Landon, R., et al., "Bridging the Gap: A case study in the validation of hybrid connectors", Process PharmaTEC International, issue Jun. 2004 (RP1007EN00), pp. 16-17, Nov. 2004, 3 pages.
ITT, Pure-Flo Hygienic diaphragm valves, actuators, and switch packages, http://www.ittpureflo.com/valvetype.html dated May 8, 2012 and Oct. 30, 2009, 12pages.
Pure-Flo: Sample and Bleed Valves for the pharmaceutical and bioprocessing industries, dated Sep. 1992, ITT Fluid Tech. Corp., (Bates stamp WLG=DEL00039389-WLG-DEL00039394), 6 pages.
Pure-Flo Solutions, Pure-Flo Radial Seated Tank Bottom Diaphragm Valve, Datasheet [online], ITT Industries, 2001 (only the year was cited on the publication), (2 pages).
Redacted email, dated Jun. 4, 2012, regarding Disposable Steam Connector, 2 pages.
Risk Free Connection of Sterilized Single-Use Fluid Path Assemblies to Stainless Steel SIP Systems with Lynx ST (Steam-To) Connectors [online], Millipore Corporation Application Note, Rev. A, Lit. No. AN7428EN00, May 2008. Retrieved from the Internet: www.millipore.com (8 pages).
Sani-Tech Globe & Angle Valve product information, dated Aug. 1989 (Bates stamp WLG-DEL00040302-WLG-DEL00040304), 3 pages.
Millipore, Series 2000, Single Sanitary Cartridge Housing, Instructions for Installation and Maintenance, Lit. No. P35265, Rev. A, Feb. 2000, 12 pages.
"Sip-Able Sample Valve," Datasheet [online]. Retrieved from the Internet: www.fluidlinetech.com (1 page), product offered online as early as Jun. 26, 2007, according to URL search performed on http://web.archive.org.
Steam-in-Place Bag Connector, http://www.fluidcomponents.net/tc_tech.html, download on Feb. 18, 2010, 1 page.
"Rapid Aseptic Fluid Transfer System Introduction" Stedim BIosystems. [online]. Retrieved from the Internet: <URL: http: www.stedim.com/p2A_IDC_introduction.php> (2 pages), dated Nov. 21, 2007.
ThermoScientific, Data Sheet 053, Rev. 2, "Aseptic Connection Devices", 2008, 2 pages.
Valves, Gemu Valves and Distributor, Diaphragm Valves, Sanitary Valves, Aseptic Valves, Valves and Fittings, Casella Sales and Marketing, Inc., http://www.casellasales.com, dated May 8, 2012 and Oct. 30, 2009, 13 pages.
Waukesha Cherry-Burrell Manual Valves, dated May 2000 (Bates stamp CSMI000044-CSMI000066), 23 pages.
Office action dated Mar. 9, 2016 in co-pending U.S. Appl. No. 13/972,301.
Office action dated Apr. 4, 2016 in co-pending U.S. Appl. No. 13/972,301.
Office action dated Apr. 18, 2014 in related U.S. Appl. No. 14/040,777.
Office action dated Mar. 20, 2015 in co-pending U.S. Appl. No. 13/827,747.
Final rejection dated Oct. 7, 2015 in co-pending U.S. Appl. No. 13/827,747.
Office action dated Jun. 1, 2016 in co-pending U.S. Appl. No. 13/827,747.
Office action dated Dec. 23, 2016 in co-pending U.S. Appl. No. 13/827,747.
Final rejection dated Jun. 28, 2017 in co-pending U.S. Appl. No. 13/827,747.
European communication dated Nov. 17, 2017 in co-pending European patent application No. 10189175.2.
Office action dated Feb. 1, 2018 in co-pending U.S. Appl. No. 13/827,747.
Final rejection dated Aug. 24, 2018 in co-pending U.S. Appl. No. 13/827,747.
Office action dated Jan. 22, 2019 in co-pending U.S. Appl. No. 13/827,747.

* cited by examiner

FLUID TRANSFER DEVICE

This application is a continuation of U.S. application Ser. No. 13/827,747 filed Mar. 14, 2013, which is a continuation of U.S. application Ser. No. 12/291,814 filed Nov. 13, 2008 (U.S. Pat. No. 8,690,120 issued Apr. 8, 2014), which claims priority to U.S. Provisional Application No. 61/003,364 filed Nov. 16, 2007, the disclosures of which are herewith incorporated by reference in their entirety.

BACKGROUND OF THE INVENTION

In the pharmaceutical, biotechnology and even food, beverage and cosmetic industries, it is often desired to provide large scale processing systems that are capable of handling fluids in a sterile manner. These large scale processing systems are designed to prevent unwanted and often dangerous organisms, such as bacteria, as well as unwanted and potentially harmful environmental contaminants, such as dust, dirt and the like from entering into the process stream and/or end product. In order to prevent these types of outside contaminants from entering these systems it is desirable to have a completely sealed processing system. However, completely closed processing systems are not always possible since there is a need for the introduction or removal of materials from the process stream in order to add components of the product, such as media or buffers to a bioreactor; withdraw samples from the process stream to check for microbial contamination, quality control, process control, etc; and to collect the product into its final container such as vials, syringes, sealed boxes, bottles and the like.

Traditionally, processing systems have been made of stainless steel, wherein the stainless steel systems are exposed to live steam before use, and then cleaned with chemicals such as caustic solutions after use, to ensure that all contaminants and the like are removed. Steaming is the most effective means of sterilization. The use of steam in a set system is known as steaming in place or SIP. Saturated steam carries 200 times the BTU heat transfer capacity of heated air because of the latent heat released by the steam as it changes from vapor to liquid.

However, several disadvantages exist with the use of steam. Any connection to, or opening of, the processing system made after the system has been steamed in place is an aseptic (but not sterile) connection or opening. This increases the risk of contamination of the entire system. Typically alcohol wipes or an open flame are used to clean the components intended to be connected to the system, (e.g., connecting a sample collection bag to a system after SIP has occurred) and thus minimizes the risk of contamination.

Also, the high temperatures and pressure differentials associated with steam make the selection of filter materials and other components difficult and limited. Additionally, accidental pressure differential at high temperatures can cause a filter, membrane or other non-steel component to fail.

Processing systems that are reused need to undergo rigorous testing and validation to prove to the necessary regulatory authorities that the system is sterile before each use. The validation process and the required cleaning regiment of a previously used system are expensive and time consuming, typically taking up to 1 to 2 years for approval. In addition, certain components are difficult to adequately clean after use in preparation for their next use. Since manufacturers are often looking for ways to reduce both the costs and the time to market for their products, one possible approach at reducing costs and time to market for a product is to adopt an all disposable system that is set up in a sterile fashion, used once and then discarded.

Another possible approach to alleviating the time and expense associated with a systems' cleaning regiment is the use of disposable components for certain reusable components that are more expensive and/or time consuming to clean than other components.

Additionally, disposable components that are used in place of time consuming to clean reusable components should be easy to remove and replace. For example, the ease with which large scale disposable fluid transfer devices, such as valves or connectors, can be removed and replaced, and the manner in which large scale disposable assemblies are integrated into traditional stainless steel processing systems via disposable fluid transfer devices, have the potential to reduce processing costs and improve the efficacy and productivity of these systems.

SUMMARY OF THE INVENTION

The present invention relates to a sterile transfer device for fluids, wherein the fluids are liquids or gases. In one embodiment, the transfer device includes a body, a bore formed through at least a portion of the interior of the body, and a linearly moveable plunger contained within the bore. In one embodiment, the bore is a lateral central bore formed through the entire interior length of the body, wherein the body is formed from a rotating first section and a stationary second section, such that the first section rotates around a portion of the stationary second section and the plunger. The rotation of the first section engages the stationary second section and the plunger, driving the plunger linearly within the bore, thereby actuating (i.e., opening/closing) the fluid transfer device. One end of the body includes a connecting component for attaching the device to an upstream component, and one end of the plunger includes a connecting component for attaching the device to a downstream component. In one embodiment, the plunger includes first and second openings, and a fluid channel in at least a portion of the interior of the plunger, connecting the first and second openings, thereby forming a pathway for fluid to travel from an upstream component to a downstream component when the fluid transfer device is in the opened position. When the device is in the closed position, the first end of the plunger is in alignment with the connecting component at one end of the body, forming a seal against fluid in the upstream component from entering the device, thereby forming a steamable face and a sterile barrier against environmental contaminants for any downstream component.

In another embodiment, the present invention relates to a fluid transfer device in use, wherein the device is in the closed position and attached to a downstream component(s), such as tubing connected to a bag, at one end of the plunger at a connecting component. Next, the entire fluid transfer device and the attached downstream component are sterilized, such as with gamma radiation or the like. Next, an upstream component (s), such as a filter outlet, a tank outlet, or a pipe is attached to a face formed at another end of the device when the device is the closed position. This face is formed when a connecting component at one end of the body is in alignment with the bottom portion. Next, the upstream component attached to the device at the face, are then steam sterilized in place (SIP). Finally, the device is then opened when needed, establishing a sterile pathway for fluids traveling from the upstream component through the fluid transfer device to the downstream component.

In another embodiment, the present invention relates to a disposable fluid transfer device for use in traditional stainless steel processing systems or disposable processing systems. The fluid transfer device of the present invention provides a steam sterilizing mating point between the transfer device and an upstream component, and a sterilizable mating point between the transfer device and a downstream component. Additionally, the transfer device can be conveniently removed from the processing system and discarded after use, thereby not requiring a cleaning regiment.

In another embodiment, the present invention also relates to disposable large scale fluid transfer devices for the integration of large scale disposable upstream and/or downstream assemblies into traditional stainless steel systems or disposable systems. The fluid transfer device of the present invention provides a steam sterilizing mating point between the transfer device and an upstream component, and a sterilizable mating point between the transfer device and a downstream component. Additionally, the transfer device can be conveniently removed from the processing system and discarded after use, thereby not requiring any cleaning regiment.

IN THE DRAWINGS

The present invention will become more fully understood from the detailed description given herein below and the accompanying drawings which are given by way of illustration only, and thus are not limitative of the present invention, and wherein.

DETAILED DESCRIPTION OF THE INVENTION

In general, the present invention is a sterile fluid transfer device, such as a flow-through connector or valve, wherein the fluids are liquids and/or gases. In one embodiment, the fluid transfer device has a body, a bore located in the interior of the body, and a linearly movable plunger contained within the bore. The body is formed from a first and a second section. The first section has a first end containing a first opening and a termination attachment component, such as a flange or the like surrounding the first opening for attaching the body to an upstream component(s). The second section has a second end containing a second opening, wherein the bore connects the first and second openings. The first section rotates around a portion of the second section.

The linearly movable plunger includes a first end containing a first opening, a second end containing a second opening, a fluid channel located in the interior of the plunger connecting the first and second openings of the plunger. In one embodiment, the plunger includes a component for inhibiting its rotation, while promoting its linear movement within the bore during rotation of the first section of the body when the device is actuated (i.e., opened/closed).

The fluid transfer device is in the closed position when the first end of the plunger is in alignment with the termination attachment component surrounding the first opening of the body, thereby forming a fluid resistant seal and a steamable face. The device is in the opened position when the first end of the plunger is not in alignment with the termination attachment component surrounding the first opening of the body, thereby permitting fluids to enter the device from an upstream component.

To the extent that the same reference numbers apply to the figures they have been kept the same.

Figures 1A, 1B:
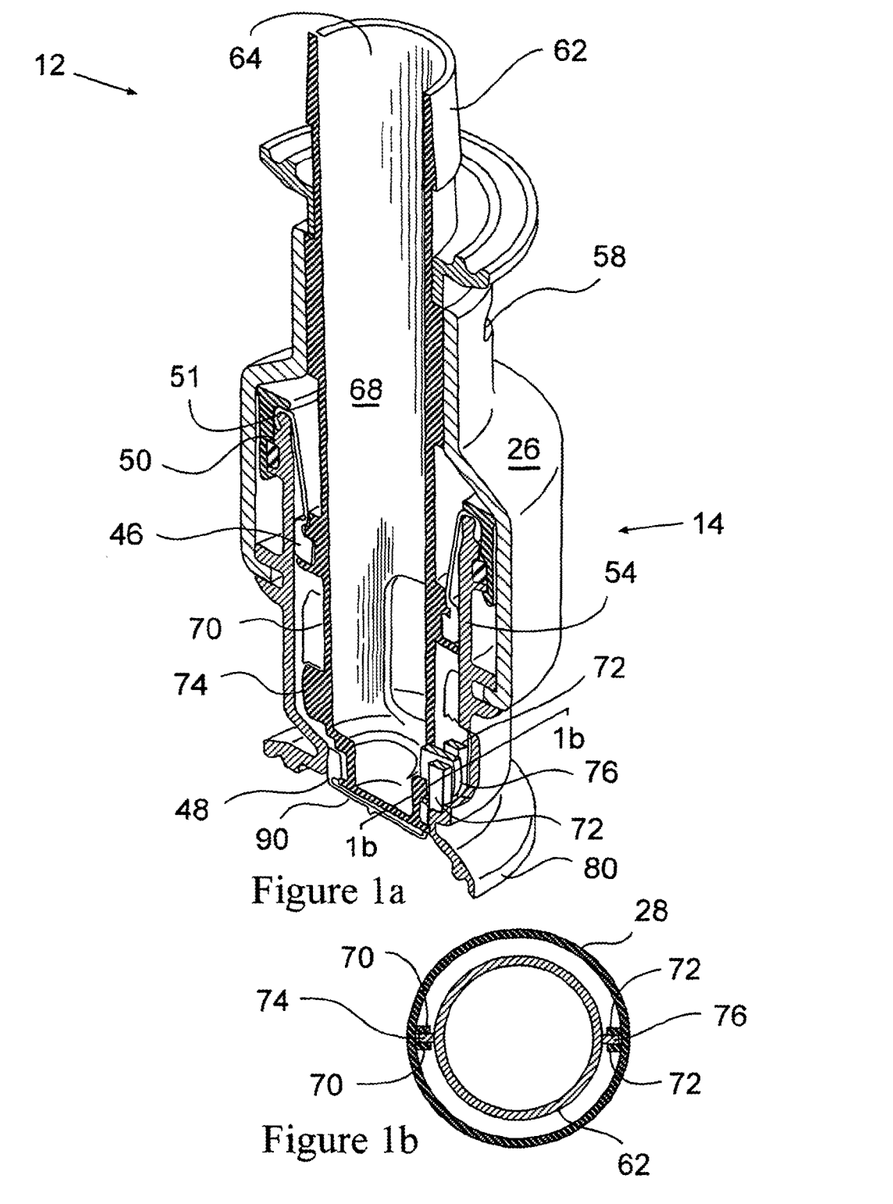
FIG. 1a is a cross sectional view of an embodiment of the present invention in a closed position.
FIG. 1b is a cross section taken along line 1b-1b.
Figure 2:
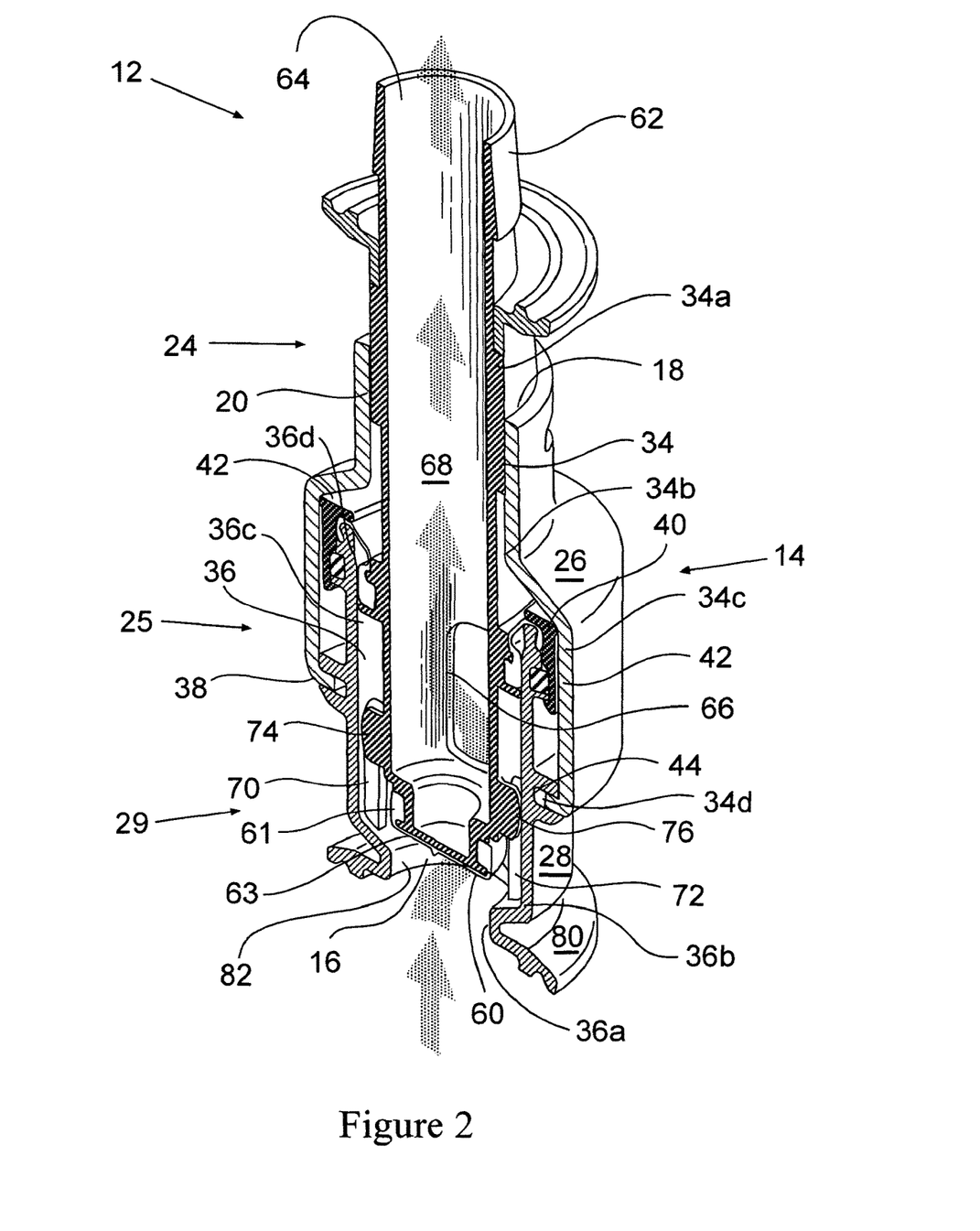
FIG. 2 is a cross sectional view of the embodiment of the present invention of FIG. 1 in an opened position.

One embodiment of the invention shown in FIGS. 1a and 2 includes a device 12 having a body 14 having a bore 20 formed through at least a portion of the interior of the body, and a generally hollow moveable plunger 62 contained within the bore. Bore 20, as shown, is a lateral central bore formed through the entire interior length of the body 14. Body 14, as shown, is formed from two sections, a rotating first section 26 and a stationary second section 28. First section 26 rotates partially around a portion of the stationary second section 28 and plunger 62. Bore 20, as shown, is formed of two sections, a rotating bore section 34 which generally corresponds to the inner wall of rotating first section 26, and a stationary bore section 36 which generally corresponds to the inner wall of stationary second section 28. In the embodiment depicted in FIGS. 1a and 2, each of the bore sections (34, 36) has different diameters. As will be described in greater detail herein, device 12 is actuated (i.e., opened/closed) when first section 26 of the body is rotated, engaging second section 28 of the body and plunger 62, driving the plunger linearly within the bore 20, thereby actuating (i.e., opening and closing) the device.

As shown in FIGS. 1a and 2, the first section 26 of the body 14 is generally hollow and has an opening 18 at one end for receiving the plunger. As shown in FIGS. 1a and 2, the first section 26 includes a protruding lip or edge component 38 that is rotatably engaged by a stationary wall receiving groove 44 on the outer stationary 28 wall section.

In FIG. 2, the first section 26 also includes an inner wall having a stationary wall engaging section 40, and forms a rotating bore section 34 having four sections. There is a first rotating bore set diameter 34a, a transition rotating bore section 34b, a second rotating bore diameter 34c and a third rotating bore diameter 34d. The first set diameter 34a engages the plunger as it moves linearly within the bore 20. The transition section 34b is arranged between the first and second diameters (34a, 34c) and has an outwardly tapering diameter along its length. The diameter of the transition section 34b is preferably a linear outward progression from the first diameter section 34a, wherein the diameter of the transition section 34b adjacent the first diameter 34a is equal to the first diameter 34a, and the diameter of the transition section 34b adjacent the second diameter 34c is equal to the diameter 34c. The third diameter 34d is preferably less than diameter 34c and preferably greater than the diameter 34a.

As shown in FIGS. 1a and 2, the stationary second section 28 of the body 14 is generally hollow and has an opening 16 at one end that permits a fluid provided from an upstream source (not shown) to pass through it when opened. The opening 16 also receives the bottom 63 of the plunger when the device is closed. The stationary section 28 includes an outer wall component 42 for rotatably engaging the inner wall section 40 of the rotating section 26. As shown in FIGS. 1a and 2 the inner wall of the second section 28 forms the stationary bore section 36 having four sections. There is a first stationary bore diameter 36a, a first transition stationary bore section 36b, a second stationary bore diameter 36c, and a second transition stationary bore section 36d. The first bore diameter 36a is less than the second bore diameter 36c. The second bore diameter 36c is a set diameter. The first transition bore section 36b is arranged between the first and second bore diameters (36a, 36c) and has an outwardly tapering diameter along its length. The diameter of the first transition section 36b is preferably a linear outward progression between the first and second bore diameters (36a, 36c). The diameter of the first transition section 36b adjacent the first diameter 36a is equal to the diameter 36a, and the diameter of the first transition section 36b adjacent the second diameter 36b is equal to the diameter 36b.

As shown in FIGS. 1a and 2 plunger 62 has three general regions comprising a first, second and third region. The first region 24 has a diameter equal to or less than the first rotating bore set diameter 34a. The second region 25 has a diameter equal to or less than the second stationary bore diameter 36c. The third region 29 has a diameter equal to or less than that of the first stationary bore diameter section 36a. The plunger has a bottom component 63 at the end of the third region 29 for blocking the opening 16 of the stationary section 28 when the device is in the closed position, as shown in FIG. 1a. One embodiment of the invention as depicted in FIGS. 1a and 2 includes a static diaphragm seal 60 located on the bottom 63 of the plunger forming a tight fluid resistant seal between the outer wall 61 of the bottom end 63 of the plunger, and the inner wall 82 of stationary section 28 of the body forming the opening 16.

Plunger 62 also has at least two openings, a first opening 64 and a second opening 66. A channel 68 is located in the interior of the plunger and connects the first and second openings (62, 64), thereby forming a fluid pathway to a downstream component. As shown in FIGS. 1a and 2, the first opening 64 is located in the first portion 24 of the plunger, and the second opening 66 is located in the second portion 25 of the plunger. In other embodiments, plunger 62 can contain additional openings and interior fluid pathways. In one preferred embodiment, the plunger contains at least openings in the second portion 25. (not shown)

One embodiment of the invention as depicted in FIGS. 1a and 2 includes plunger 62 having a component for inhibiting the rotation of the plunger within the bore, while promoting linear movement of the plunger when the fluid transfer device 12 is actuated (i.e., opened/closed). One embodiment for accomplishing the linear movement of the plunger, as shown in FIGS. 1a and 2, depicts the plunger having a pair of wings (74, 76), fins, or the like, that extend from the outer wall of the plunger towards the inner wall of the second section 28 of body 14. Second section 28 has a component for interacting with wings (74, 76) comprising two corresponding pairs of parallel slots (70, 72), grooves, or the like located on the inner wall of the section 28 for receiving the wings (74, 76) in order to restrict the rotation of the plunger 62 and promote the linear movement of the plunger within the bore 20. Wings (74, 76) ride between each corresponding pair of slots (70, 72) thereby facilitating the linear movement of the plunger within the bore during actuation (opening/closing) of the device 12.

As shown in FIG. 1a, when device 12 is in the closed position the bottom end 63 of the plunger is in alignment with flange 80, forming a face 90, and providing the device with a steamable surface and a sterile barrier against the environment for the interior of the device, plunger and any downstream components. In the closed position, the bottom end 63 of the plunger does not permit fluid to enter opening 16 in the device from an upstream component (not shown), thereby preventing any fluid from traveling downstream.

As shown in FIG. 2, device 12 is in the opened position when the plunger 62 is linearly moved within the lateral bore 20 by the rotation of section 26 of the body 14, such that the bottom end 63 of the plunger 62 is moved back from the flange 80, permitting fluid, depicted by an arrow, to travel from an upstream component (not shown), through opening 16 in section 28 of the body. The fluid then travels through the second hole 66 of the plunger, into the interior channel 68 of the plunger, out opening 64, and into a downstream component. (not shown) Plunger 62 is not permitted to rotate within the bore during the rotation of the rotating section 26, but is forced to move linearly by wings (74, 76) of the plunger located within the parallel slots (70, 72) on the inner wall of section 28.

Additionally, by preventing the plunger from rotating when the device is opened or closed, the problem of torsion between device 12 and an attached upstream or downstream component can be averted, since it is not necessary to twist or turn the upstream or downstream components, or the device, when removing or actuating the device since the plunger moves within the bore linearly, and not rotationally.

Figure 3A:
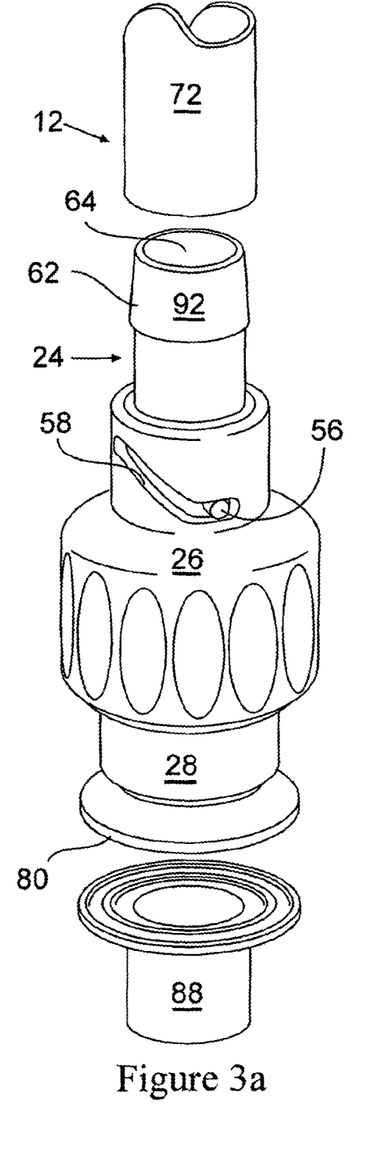
FIGS. 3a and 3b are perspective views of additional embodiments of the present invention of FIG. 1, along with alternative embodiments of upstream and downstream attachment components.
Figure 3B:
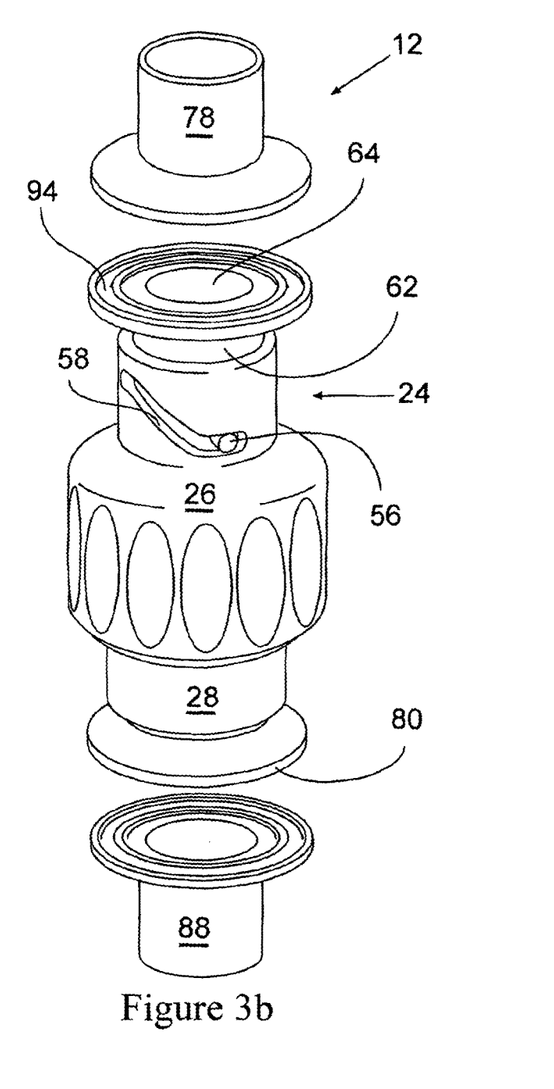
Figure 4A:
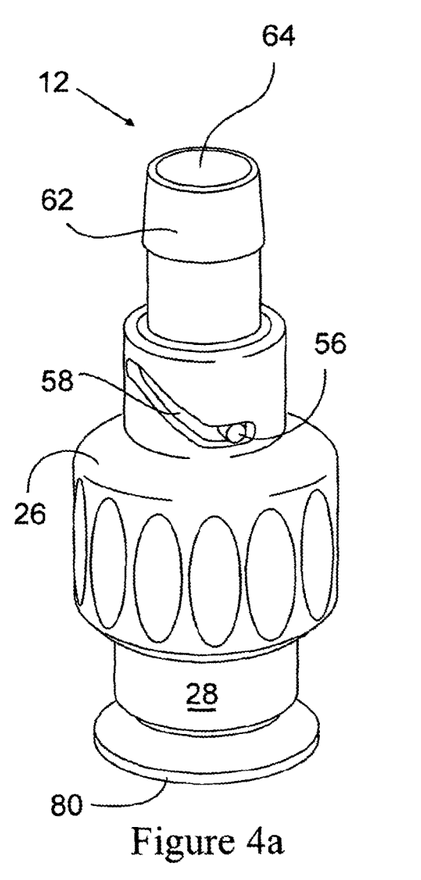
FIGS. 4a and 4b are perspective views of an embodiment of the present invention of FIG. 1.
Figure 4B:
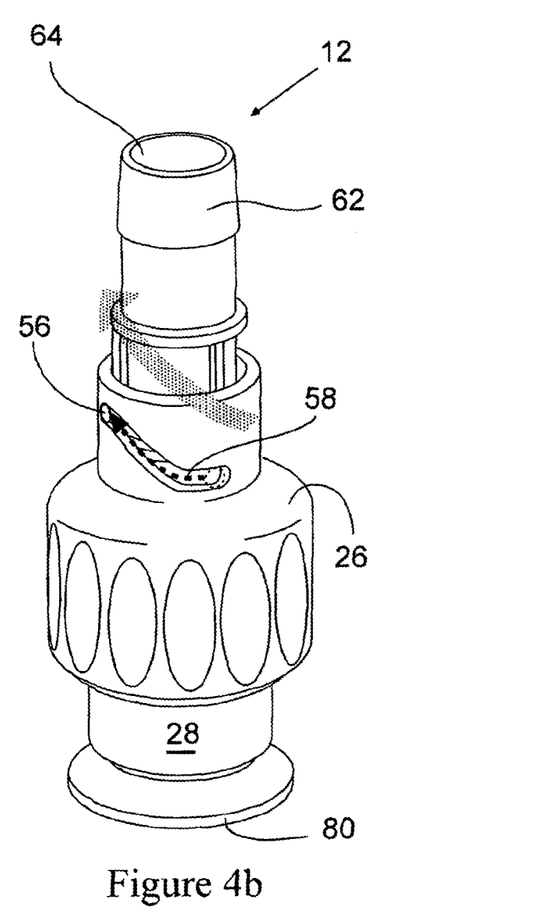

As shown in FIGS. 3a, 3b, 4a, and 4b, the plunger 62 can contain one or more cams 56 (only one shown) that ride in one or more cam slots 58 (only one shown) located in the rotating section 26 of the body 14. The arrangement of the cam 56 and slot 58 acts to limit the length the plunger 62 travels linearly within the bore 20 when the device is actuated (opened or closed). When device 12 is in the closed position, as shown in FIG. 4a, the cam 56 sits in the closed position of the cam slot 58. When device 12 is in the opened position, as shown in FIG. 4b, the cam 56 sits in the opened position of the calm slot 58. The arrow in FIG. 4b depicts the rotational movement of rotating section 26 and cam slot 58.

As shown in FIGS. 3a and 3b, device 12 has at one end of the stationary section 28 of the body a component for attaching the device to an upstream component. In this embodiment, a flange 80 attaches to a flange 88 of an upstream component. As shown in FIG. 3a, the end of the first plunger region 24 includes, in this embodiment, a barb termination 92 for connecting the device to a downstream component, in this instance, tubing 72.

As shown in FIG. 3b, the end of first plunger portion 24 includes, in this embodiment, a termination flange 94 for connecting the device to a downstream component, in this embodiment, a termination flange 78.

By way of example, the downstream components attached to the device by the termination connection feature on the plunger can be plastic tubing 72 and the like, as shown in FIG. 3a, attached to a plastic bag or other type of known receptacle (not shown), and the like.

By way of example, the upstream component attached to the device can be a pipe, a stainless steel or disposable plastic tank having an outlet, and the like, having an attachment flange 88 (as depicted in FIGS. 3a and 3b), or any other mode of attachment for connecting components to transfer devices as are commonly known in the art. For example, flange 80 on device 12 can be connected to an upstream component or pipe by a clamp such as a Tri-Clover™ fitting, Ladish™ fitting, ClickClamp™ clamp and the like.

When using device 12 to fill a downstream component such as a bag, or any collection vessel attached the tubing 72, the device is opened by rotating section 28 of the body, which moves the plunger 62 linearly (see FIG. 4b) away from the face 90, permitting fluid to enter opening 16 (see FIG. 2) and to eventually flow out the opening exit 64 through tube 72, and into a bag, or any collection vessel or other fluid transport device. (not shown) Once a bag is full, the rotating section 28 is rotated in the opposite direction to move the plunger linearly again, this time in the opposite direction, in order to seal the opening 16 closed (see FIG. 1) to the fluid from an upstream component. By way of example, an attached bag can then be closed off via a clamp or hemostat (not shown) and removed for further processing or use.

One or more seals are arranged along the length and end of the plunger 62 to form a fluid tight seal between various portions of the plunger 62 and the bore 20 when the device is in the closed or opened positions. As shown in FIGS. 1a and 2, seals 60 and 54 are partly contained within grooves 48, and 46 and 44 respectively.

As shown in FIGS. 1a and 2, the seals may be mounted on the plunger 62. However, if desired, a different configuration of seals and their placements can also be used. For example, FIGS. 1a and 2 show seals 46 and 60 formed in grooves on the plunger 62. A linear or gland seal 51 is retained within a groove 50 on the inner wall of the stationary bore section and within a groove 46 on the plunger 62.

Other embodiments of the present invention are also contemplated, such as molding the device 12 into a disposable plastic container such as a disposable process bag for the manufacture and transfer of biotech products and the like. Such bags are readily available from companies such as HyClone (which is part of Thermo Fisher Scientific) of Logan, Utah and Stedim Biosystems of Concord, Calif.

Since the fluid transfer device 12 is preferably provided in a sterile condition, (i.e., the interior of the system and any component connected downstream of the device is pre-sterilized such as with gamma radiation, ethylene gas or the like and shipped in a sterile condition), some type of use indicator (not shown) may be helpful, and capable of informing a user when a system has been used. As an alternative, or in addition to any of the indicator mechanisms discussed above, a shrink wrap indicator (not shown) may be located over the device or at least over the rotating first section of the device to indicate whether the device had been used.

The device is preferably formed a plastic material and may be formed by machining the body and plunger assemblies and then applying the necessary seals and the like, or preferably by molding the body and the plunger separately and assembling them together with the necessary seals and other components. Alternatively, the body may be molded into two separate halves and assembled by attaching the plunger component with the necessary seals and other components to one half of the body, followed by the attaching the remaining half of the body to the plunger, necessary seals, other components, and the first half of the body.

The device may be made of any plastic material capable of withstanding in line steam sterilization. The temperature and pressure of such sterilization is typically about 121° C. and 1 bar above atmospheric pressure. In some instances, it may be desirable to use even harsher conditions such as 142° C. and up to 3 bar above atmospheric pressure. The body and at least the face of the plunger should be capable of withstanding these conditions. Preferably, the entire device is made of the same material and is capable of withstanding these conditions. Suitable materials for this device include but are not limited to PEI (polyetherimide), PEEK, PEK, polysulphones, polyarlysulphones, polyalkoxysulphones, polyethersulphones, polyphenyleneoxide, polyphenylene-sulphide and blends thereof. Alternatively, one can make the face portion from ceramic or metal inserts alone, or that are overmolded with a plastic cover. One can also form a polymeric face with a metal outer layer using plasma coating processes.

The seals of the present invention can be made of a variety of materials typically used for making resilient seals. These materials include but are not limited to natural rubber, synthetic rubbers, such as silicone rubbers, including room temperature vulcanizable silicone rubbers, catalyzed (such as by platinum catalysts) silicone rubbers and the like, thermoplastic elastomers such as SANTOPRENE® elastomers, polyolefins such as polyethylene or polypropylene, especially those containing gas bubbles introduced either by a blowing agent or entrained gas such as carbon dioxide, PTFE resin, thermoplastic perfluoropolymer resins such as PFA and MFA resins available from Ausimont, USA Inc., of Thorofare, N.J. and E.I. DuPont de Nemours of Wilmington, Del., urethanes, especially closed cell foam urethanes, KYNAR® PVDF resin, VITON® elastomer, EPDM rubber, KALREZ resin and blends of the above.

Suitable materials for molded in place seals can be curable rubbers, such as room temperature vulcanizable silicone rubbers, thermoplastic elastomers such as SANTO-PRENE® elastomers, polyolefins such as polyethylene or polypropylene, especially those containing gas bubbles introduced either by a blowing agent or entrained gas such as carbon dioxide and elastomeric fluoropolymers.

Other materials used in the devices should also be FDA grade components such as FDA grade silicones, PTFE resins and the like.

The present invention provides a sterile and steam sterilizable in place connecting device for fluid transfer. It may be single actuation (one open one close) or it may be multiple actuations with a single sterile connection (multiple openings and closings) so long as the sterile connection upstream and downstream is maintained. Additionally, with the use of multiple seals or seals of long length, one is able to ensure that the sterility of the device is maintained even with multiple actuations.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A fluid transfer device comprising:
a body;
an elongate passage having an interior wall and extending through the body and having a proximal end and a distal end;
a longitudinally displaceable plunger disposed in and extending along the passage, the plunger having a proximal end and a distal end and having a first position displaced toward the distal end of the passage and a second position displaced toward the proximal end of the passage;
at least one static diaphragm seal mounted on the proximal end of the plunger to form a fluid tight seal between the plunger and the passage, said static diaphragm seal remaining intact during movement of said plunger from said first position to said second position and back to said first position;
a gland seal; and
a fluid transfer opening positioned between the proximal end of the plunger and the distal end of the plunger;

wherein the body comprises a first section and a second section, wherein rotation of the first section relative to the second section causes longitudinal displacement of the plunger, and wherein the longitudinal displacement of the plunger towards its first position opens the passage to form a substantially aseptic fluid pathway from an upstream component to a downstream component through the fluid transfer opening and a channel in the interior of the plunger; and wherein the gland seal is arranged along a length of the plunger, a first portion of the gland seal being retained within a groove on a surface of the first section of the body and a second portion of the gland seal being retained within a groove on the plunger, and wherein the gland seal stretches to accommodate the displacement of and maintain a seal about the plunger.

2. The device of claim 1, wherein the diaphragm seal is attached to the proximal end of the plunger and seals the passage at the proximal end thereof.

3. The device of claim 2, wherein the diaphragm seal is disposed at least partially inside the proximal end of the passage prior to displacement of the plunger.

4. The device of claim 1, wherein the gland seal seals the passage at a location intermediate the diaphragm seal and the distal end of the passage.

5. The device of claim 1, wherein the plunger extends through and is sealingly secured to the gland seal.

6. The device of claim 1, further comprising a substantially aseptic tank mount.

7. The device of claim 1, wherein the at least one seal is constructed of a silicone elastomer.

8. The device of claim 1, wherein the at least one seal is constructed of a solvent resistant fluoroelastomer.

9. The device of claim 1, wherein the body comprises a substantially cylindrical outer portion, and at least one alignment slot for the plunger.

\* \* \* \* \*